(12) United States Patent
DiAntonio et al.

(10) Patent No.: US 8,754,060 B2
(45) Date of Patent: Jun. 17, 2014

(54) METHODS AND COMPOSITIONS FOR INHIBITION OF AXONAL DEGENERATION BY MODULATION OF THE DLK/JNK PATHWAY

(71) Applicant: Washington University, Saint Louis, MO (US)

(72) Inventors: Aaron DiAntonio, Olivette, MO (US); Bradley R. Miller, St. Louis, MO (US); Jeffrey D. Milbrandt, Clayton, MO (US); Craig A. Press, St. Louis, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/722,821

(22) Filed: Dec. 20, 2012

(65) Prior Publication Data

US 2013/0203838 A1 Aug. 8, 2013

Related U.S. Application Data

(62) Division of application No. 12/548,411, filed on Aug. 26, 2009, now abandoned.

(60) Provisional application No. 61/091,976, filed on Aug. 26, 2008.

(51) Int. Cl.
| | | |
|---|---|---|
| *C12N 15/11* | (2006.01) |
| *C12Q 1/68* | (2006.01) |
| *C07H 21/02* | (2006.01) |
| *C07H 21/04* | (2006.01) |
| *C12N 5/02* | (2006.01) |
| *C12N 5/00* | (2006.01) |

(52) U.S. Cl.
USPC ......... 514/44 A; 435/6.11; 435/325; 435/375; 536/23.1; 536/24.5

(58) Field of Classification Search
None
See application file for complete search history.

(56) References Cited

U.S. PATENT DOCUMENTS

| 2004/0087642 A1* | 5/2004 | Zeldis et al. | 514/406 |
| 2004/0176434 A1* | 9/2004 | Bennett et al. | 514/406 |
| 2006/0172991 A1* | 8/2006 | Fleenor et al. | 514/211.08 |

FOREIGN PATENT DOCUMENTS

WO    WO 00/13015    *    3/2000

* cited by examiner

*Primary Examiner* — Doug Schultz
(74) *Attorney, Agent, or Firm* — Saul L. Zackson; Zackson Law LLC (57) ABSTRACT

Methods of reducing Wallerian degeneration are disclosed. These methods comprise inhibiting expression or activity of a mixed lineage kinase such as a dual leucine-zipper-bearing kinase (DLK), inhibiting expression or activity of a molecule acting downstream from DLK, such as a c-Jun N-terminal kinase (JNK), or a combination thereof. Further disclosed are methods of screening candidate compounds for DLK inhibition activity. These methods comprise providing a neuronal culture comprising a plurality of axons; contacting the culture with a candidate compound and with an axon degeneration-triggering agent; and comparing axonal degeneration in the culture to a control culture comprising the axon degeneration-triggering agent but not the candidate compound.

5 Claims, 4 Drawing Sheets

METHODS AND COMPOSITIONS FOR INHIBITION OF AXONAL DEGENERATION BY MODULATION OF THE DLK/JNK PATHWAY

CROSS-REFERENCE TO RELATED APPLICATIONS

This application is a Divisional of U.S. Non-provisional application Ser. No. 12/548,411 filed on Aug. 26, 2009 which claims priority to U.S. Provisional Application Ser. No. 61/091,976 filed on Aug. 26, 2008. These applications are incorporated herein by reference, each in its entirety.

STATEMENT REGARDING FEDERALLY SPONSORED RESEARCH OR DEVELOPMENT

The disclosed subject matter was developed in part with Government support under grants NS040745 and AG013730 from the National Institutes of Health. The Government has certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

Axon degeneration is a common feature of many neurological ailments including mechanical injury, exposure to neurotoxins, hereditary neuropathies, glaucoma, and neurodegenerative diseases such as Alzheimer's Disease and Parkinson's Disease (Coleman, M. P., et al., Trends Neurosci. 25:532-537 (2002); Luo, L., et al. Ann. Rev. Neurosci. 28: 127-156 (2005); Saxena, S., et al., Prog. Neurobiol. 83: 174-191 (2007)). Axon loss is a direct cause of neurological impairment and it also often proceeds and promotes cell body dysfunction and death. Despite the diversity of insults that lead to axon loss, axons tend to degenerate following a stereotyped progression of morphological changes. This breakdown process, termed Wallerian degeneration and first described in the 1850s, is hypothesized to be an active and highly regulated process (Coleman, M., et al. Nat. Rev. Neurosci. 11: 889-898 (2005); Raff, M. C., et al., Science. 296: 868-871 (2002)).

A wide range of insults appear to trigger a common axon self-destruction program. For example, pharmacological inhibition of the ubiquitin proteasome system (Zhai, Q., et al., Neuron 39: 217-225 (2003); MacInnis, B. L., Mol. Cell Neurosci. 3: 430-439 (2005); Hoopfer, E. D., et al., Neuron 50: 883-895 (2006)), calpain proteases (George, E. B., et. al., J. Neurosci. 15: 6445-6452 (1995); Spira, M. E., et al., J. Comp. Neurol., 457: 293-112 (2003); Wang, M. S., et al., Brain 127: 671-679 (2004); Touma, E., et al., Eur. J. Neurosci. 26:3368-3381(2007)), and trypsin-like proteases (Ikegami, K., et al., Brain Res. 1030: 81-93 (2004)) decrease Wallerian degeneration. Preventing rises in $Ca^{2+}$ can also be protective (Stys, P. K., J. Neurol. Sci. 233: 3-13 (2005)). Finally, over-expression of the chimeric protein Wld$^s$ (Mack, T. G., et al., Nat. Neurosci. 4:1199-1206 (2001)) and nicotinamide mononucleotide adenylyltransferase (Nmnat) (Araki, T., et al., Science. 305: 1010-1013 (2004)) dramatically delays axon degeneration in response to multiple insults. Thus, diverse neuronal insults appear to trigger a common self-destruction mechanism within the axon.

Wallerian degeneration is conceptually similar to but distinct from apoptosis: each appears to be an intrinsic process that is primed and waiting for a triggering stimulus to activate the execution phase. Degenerating axons have been shown to exhibit to microtubule depolymerization, altered axonal transport, mitochondrial dysfunction, increased reactive oxygen species, phosphatidylserine exposure, membrane blebbing, and axon fragmentation (Coleman, M. P., et al., Trends Neurosci. 25: 532-537(2002); Luo L., et al., Ann. Rev. Neurosci. 28: 127-156 (2005); Saxena S., et al., Prog. Neurobiol. 83:174-191 (2007); Coleman, M., Nat. Rev. Neurosci. 11: 889-898 (2005); Raff, M. C., et al., Science. 296: 868-871(2002)). Although many of these pathological changes are shared with neuronal apoptosis, the molecular pathways are distinct. A variety of manipulations that block neuronal apoptosis do not prevent. Wallerian degeneration (Finn, J. T., et al., J. Neurosci. 20: 1333-1341 (2000); Sagot, Y., et al., J. Neurosci. 15: 7727-7733 (1995); Whitmore, A. V., et al., Cell Death Differ. 10: 260-261 (2003)).

Although inhibition of the effectors of neuronal apoptosis does not decrease axon degeneration, some upstream regulators of these effectors are highly expressed in axons and are activated by axonal insults. Such upstream regulatory molecules include members of the mixed lineage kinase (MLK) family, such as dual leucine-zipper-bearing kinase (DLK). DLK is a mitogen activated protein kinase kinase kinase (MAP3K) involved in axonal transport (Horiuchi, D., et al., Curr. Biol. 17: 1311-1317 (2007)), axon pathfinding (Hirai, S. et al., J. Neurosci. 26: 11992-12002 (2006)), neuronal migration (Hirai, S., et al., J. Neurosci. 26: 11992-12002(2006)), and neuronal apoptosis. DLK activates the MAP kinases JNK and/or p38 in a variety of systems (Gallo. K. A., et al., Nat. Rev. Mol. Cell Biol. 3: 663-672 (2002)). Interestingly, one of DLK's downstream targets, the mitogen activated protein kinase (MAPK) C-Jun N-terminal kinase (JNK), is activated locally in axons following injury (Cavalli, V., et al., J. Cell Biol. 168: 775-787 (2005)).

Many insults, such as trophic withdrawal and axotomy, can induce both neuronal apoptosis and axon degeneration. Axon degeneration can also be triggered by a range of insults that are relevant to human disease. Inhibitors of axotomy-induced degeneration often also decrease axon loss in mouse models of these diseases, implying that a common axon self-destruction pathway is employed (Coleman, M. P., et al., Trends Neurosci. 25: 532-537 (2002); Coleman, M., Nat. Rev. Neurosci. 11: 889-898 (2005)). For example, vincristine is a chemotherapeutic drug that inhibits microtubule formation, and whose dose-limiting side effects in patients include peripheral neuropathy due to axon degeneration (Casey, E. B., et al. Brain 96: 69-86 (1973). In cultured DRG neurons, applying vincristine triggers an axon degeneration that is morphologically similar to that induced by axotomy (Wang M. S., et al., J. Neuropathol. Exp. Neurol. 59: 599-606 (2000)).

Methods of reducing, inhibiting, or preventing axonal degeneration are thus needed in many situations, such as when a subject receives cancer chemotherapy.

SUMMARY

In view of the need for methods for reducing, inhibiting, mitigating or preventing axonal degeneration, the present inventors have developed methods of treating and preventing neuropathies, axonopathies and other conditions involving axonal degeneration.

In various configurations, a neuropathy that includes axonal degeneration can be hereditary or congenital. In some configurations, a neuropathy that includes axonal degeneration can be a neuropathy associated with neurodegenerative disease, motor neuron disease, neoplasia, endocrine disorder, metabolic disease, nutritional deficiency, atherosclerosis, an autoimmune disease, mechanical injury, chemical or drug-induced injury, thermal injury, radiation injury, nerve compression, retinal or optic nerve disorder, mitochondrial dysfunction, a progressive dementia demyelinating disease, ischemia, stroke, an infectious disease, or an inflammatory disease. In some configurations, the present methods can be used to prevent or mitigate axonal degeneration that is induced by a cytotoxic anticancer agent such as, without limitation, vincristine. In some configurations, the present methods can be used to prevent or mitigate axonal degeneration associated with an optic nerve disorder, such as, without limitation, glaucoma, retinal ganglion degeneration, optic neuritis, optic degeneration, macular degeneration, ischemic optic neuropathy, traumatic injury to the optic nerve, hereditary optic neuropathy, metabolic optic neuropathy, neuropathy due to a toxic agent, a neuropathy caused by an adverse drug reaction or a neuropathy caused by vitamin deficiency. In some configurations, a mitochondrial dysfunction associated with a neuropathy can be a mitochondrial dysfunction resulting from oxidative damage, from one or more mutations in mitochondrial proteins encoded either in the mitochondrial genome or nuclear genome, from exposure to toxins, and/or from the process of aging.

In various aspects of the present teachings, methods for reducing, inhibiting, or preventing axonal degeneration can comprise methods that reduce activity of one or more enzymes of the mixed lineage kinase (MLK) family, such as dual leucine-zipper-bearing kinase (DLK), and/or a downstream target of DLK, such as a c-Jun N-terminal kinase (JNK). In various embodiments, methods of present teachings can comprise administering to a mammalian subject in need thereof, at least one inhibitor of at least one MLK and/or at least one inhibitor of at least one JNK, in an amount effective to inhibit MLK activity and/or MLK expression and/or JNK activity and/or JNK expression, in diseased and/or injured neurons and/or supporting cells. In some configurations, an MLK can be dual leucine-zipper-bearing kinase (DLK). In some configurations, a JNK can be JNK1, JNK2 or JNK3. In various configurations, a neuropathy can comprise an axonopathy, such as Wallerian degeneration.

In some configurations, a JNK inhibitor can be a selective inhibitor of a c-Jun N-terminal kinase (JNK), such as SP600215 (Anthra[1,9-cd]pyrazol-6(2H)-one; 1,9-pyrazoloanthrone) (Calbiochem., La Jolla, Calif.). In some alternative configurations, an inhibitor can be an inhibitory RNA such as an siRNA directed against expression of an enzyme such as an MLK or a JNK. In some configurations, an inhibitor can be an inhibitory RNA such as an siRNA directed against expression of DLK. In some configurations, an inhibitor can be an inhibitory RNA such as an siRNA directed against expression of a JNK, such as JNK1, JNK2 or JNK3.

In some embodiments, such as when a mammalian subject has an optic disorder, methods of the present teachings can comprise intraocular administration of a kinase inhibitor to the subject. In various configurations, intraocular administration can entail administering an enzyme inhibitor via a sustained release delivery system, by intravitrial injection, by eyedrops or by trans-scleral deliver. In various configurations of the present teachings, a mammalian subject can be a human, such as a subject in need of treatment.

In various aspects of the present teachings, the inventors disclose methods of screening candidate agents such as compounds or salts thereof for treating or preventing a neuropathy comprising axonal degeneration or axonopathy, such as Wallerian degeneration. In various embodiments, these methods can comprise contacting, in vitro or in vivo, at least one mammalian cell that expresses at least one member of the mixed lineage kinase (MLK) family such as dual leucine-zipper-bearing kinase (DLK) with a candidate agent, and detecting a decrease in MLK activity in the cell, such as a decrease in DLK activity in the cell. In other embodiments, these methods can comprise contacting, in vitro or in vivo, at least one mammalian cell that expresses at least one MLK and at least one C-Jun N-terminal kinase (JNK) with a candidate agent, and detecting a decrease in activity of the at least one MLK or the at least one JNK activity in the cell.

In various configurations, a mammalian cell of these embodiments can be a neuron, such as, without limitation, a dorsal root ganglion neuron. A neuron of these embodiments can be from any mammalian source, such as a rodent, including a rat or mouse. In addition, in various configurations, an MLK can be dual leucine-zipper-bearing kinase (DLK). Furthermore, a JNK can be a JNK1, a JNK2 or a JNK3.

In some aspects, the present teaching include methods of screening candidate compounds for activity as inhibitors of activity or expression of at least one mixed lineage kinase (MLK) and/or at least one JNK in neurons. In various embodiments, these methods comprise administering a candidate agent to mammalian neuronal cells in vitro or in vivo, producing an axonal injury to the neuronal cells, and detecting a decrease in axonal degeneration of the injured neuronal cells. These embodiments can further comprise detecting a reduction in activity of an MLK and/or a JNK. In various configurations, an MILK can be a dual leucine-zipper-bearing kinase (DLK), and a JNK can be a JNK1, a JNK2 or a JNK3.

In some aspects, the present teaching include methods of screening a candidate compound for activity as an inhibitor of axonal degeneration. In various embodiments, these methods comprise providing a plurality of *Drosophila* flies expressing a reporter in olfactory receptor neurons (ORN's), wherein the ORN's comprise axons which extend into lobes connected by a commissure; severing one or more antennae from the flies; administering a candidate compound to the flies; and scoring the *Drosophila* for presence or absence of the commissure, whereby the presence of the commissure indicates that the compound has activity as an inhibitor of axonal degeneration. In various configurations, the reporter can be a fluorescent protein, such as, without limitation, a green fluorescent protein (GFP).

In some aspects, the present teaching include methods of screening a candidate compound for activity as an MLK inhibitor. In various configurations, these methods comprise providing a neuronal culture comprising a plurality of axons; contacting the culture with a candidate compound and with an axon degeneration-triggering agent; and comparing axonal degeneration in the culture to a control culture comprising the axon degeneration-triggering agent but not the candidate compound.

In various configurations of these methods, the MLK inhibitor can be a DLK inhibitor, and a neuronal culture can comprise dorsal root ganglion neurons, such as murine dorsal root ganglion neurons. Furthermore, in various configurations, the axon degeneration-triggering agent can be a cancer chemotherapeutic, such as, without limitation, vincristine.

In some aspects, the present teaching include methods of screening a candidate compound for activity as an MLK inhibitor. In various configurations, these methods comprise providing a neuronal culture comprising a plurality of axons; axotomizing neurons comprised by the culture; contacting the culture with a candidate compound; and comparing axonal degeneration in the culture to a control culture comprising axotomized neurons but not the candidate compound. In various configurations of these methods, the MLK inhibitor can be a DLK inhibitor. A neuronal culture of these configurations can be a mammalian neuronal culture such as a murine neuronal culture. Furthermore, a neuronal culture of these aspects can comprise dorsal root ganglion neurons. In some configurations, contacting a neuronal culture with a candidate compound can comprise contacting the culture with a candidate compound within 3 hours after the axotomizing.

In some aspects, the present teaching include methods of treating a cancer. In various configurations, these methods comprise administering to a subject in need of treatment a) a chemotherapeutic pharmaceutical and b) an inhibitor of an MLK activity and/or expression, an inhibitor of a JNK activity and/or expression, or a combination thereof, in an amount effective to inhibit axonal degeneration. In various configurations, the MLK activity and/or expression can be DLK activity and/or expression, and the JNK activity and/or expression can be activity and/or expression of JNK1, JNK2 and/or JNK3. In various embodiments of these methods, the chemotherapeutic pharmaceutical can be administered in an amount greater than the amount administered without the inhibitor of the MLK activity or expression, the inhibitor of the JNK activity or expression, or a combination thereof.

In various configurations of these methods, the chemotherapeutic pharmaceutical can be comprised by a pharmaceutical composition. In addition, the pharmaceutical composition can further comprises an inhibitor of MLK activity or expression, an inhibitor of JNK activity or expression, or a combination thereof. A chemotherapeutic pharmaceutical can be any chemotherapeutic pharmaceutical known to skilled artisans, such as, without limitation, vincristine or taxol. In addition, an inhibitor of JNK activity can be SP600215, and an inhibitor of expression of an MLK can be an siRNA against expression at least one MLK. In some configurations, the MLK can be DLK. In some other configurations, the inhibitor of a JNK expression can be an siRNA against expression of at least one JNK, which can be, without limitation, JNK1, JNK2 or JNK3.

In some aspects, the present teaching include methods of treating or slowing progression of a peripheral neuropathy. In various embodiments, these methods comprise administering to a subject in need of treatment an inhibitor of an MLK activity or expression, an inhibitor of JNK activity or expression, or a combination thereof, in an amount effective to inhibit axonal degeneration. In various embodiments, an inhibitor of an MLK activity or expression can be an inhibitor of DLK activity or expression, such as, without limitation, an siRNA against DLK expression. In various embodiments, an inhibitor of an JNK activity or expression can be an inhibitor of activity or expression of JNK1, JNK2 and/or JNK3, such as, without limitation, SP600215.

In some aspects, the present teaching include methods of treating or slowing progression of a neurodegenerative disease. These methods comprise administering to a subject in need of treatment, an inhibitor of MLK activity or expression, an inhibitor of JNK activity or expression, or a combination thereof, in an amount effective to inhibit axonal degeneration. In various embodiments, an inhibitor of an MLK activity or expression can be an inhibitor of DLK activity or expression, such as, without limitation, an siRNA against DLK expression. In various embodiments, an inhibitor of an JNK activity or expression can be an inhibitor of activity or expression of JNK1, JNK2 and/or JNK3, such as, without limitation, SP600215.

In some aspects, the present teaching include methods of preserving retinal ganglion cells and/or vision in a subject with glaucoma. In various embodiments, these methods comprise administering to the subject an effective amount of an inhibitor of an MLK activity or expression, an inhibitor of a JNK activity or expression, or a combination thereof. In various configurations of these methods, an inhibitor of MLK activity or expression can be an inhibitor of DLK activity or expression such as an siRNA directed against DLK expression. In some configurations, an inhibitor of JNK activity or expression can be an inhibitor of activity or expression of JNK1, JNK2 and/or JNK3, such as JNK activity inhibitor SP600215, or an siRNA directed against expression of a JNK.

In some aspects, the present teaching include methods of protecting axons and/or neuronal function post injury. In various configurations, these methods comprise administering to a subject post injury, an inhibitor of an MLK activity or expression, an inhibitor of JNK activity or expression, or a combination thereof, in an amount effective to inhibit axonal degeneration. In various configurations of these methods, an inhibitor of MLK activity or expression can be an inhibitor of DLK activity or expression such as an siRNA directed against expression of all MLK such as DLK. In some configurations, an inhibitor of JNK activity or expression can be an inhibitor of activity or expression of JNK1, JNK2 and/or JNK3 such as JNK activity inhibitor SP600215, or an siRNA directed against expression of a JNK.

DETAILED DESCRIPTION

The identification of a signaling pathway that promotes axon degeneration opens new avenues for the development of therapies aimed at minimizing axon loss and the resulting neurological disability. The present inventors have developed methods for mitigating axonopathies that can occur in various diseases and injuries, such as optic nerve disorders. These methods are based upon inhibition of activity or inhibition of expression of kinase enzymes that contribute to the DLK/JNK pathway in neurons. The methods comprise administering to a subject an inhibitor of expression or activity of at least one mixed lineage kinase (MLK) family member, such as dual leucine-zipper-bearing kinase and/or expression or activity of at least one c-Jun N-terminal kinase (JNK) such as JNK1, JNK2 or JNK3.

In some aspects, an inhibitor can be an inhibitory RNA such as a small interfering RNA (siRNA) that inhibits expression of a protein component of the DLK/JNK pathway, such as an MLK family member such as dual leucine-zipper-bearing kinase (DLK), or a c-Jun N-terminal kinase (JNK), such as JNK1, JNK2 or JNK3. An siRNA that can be used in the methods disclosed herein can have a sequence which is selected and synthesized according to methods well known to skilled artisans, or can have a structure that has already been shown to inhibit kinase activity. In non-limiting example, an siRNA can be an siRNA that inhibits expression of DLK, such as a STEALTH RNAi™ (Invitrogen, Carlsbad, Calif.) siRNA that inhibits DLK expression (Plaumann, S., et al., Mol Pharmacol 73: 652-659, (2008)). In another non-limiting example, an siRNA can be an siRNA that inhibits expression of an MLK, such as described by Chadee et al. ((Chadee, D. N., et al., Proc. Nat'l. Acad. Sci. USA 103: 4463-4468 (2006); Chadee, D. N., et al., Nat. Cell Biol. 6: 770-776 (2004)), or available from a supplier such as Dharmacon RNA Technologies (Lafayette, Colo.). Some non-limiting examples of RNAi that inhibit JNK expression include: Jnk1/2 siRNA 5'-GAAUGUCCUACCUUCUCUA-3' (SEQ ID NO 1); JNK 1 pool siRNA 5'-GGAAAGAACUGAUAUACAA-3'(SEQ ID NO 2) and 5'-GAAGCAAACGUGACAACAA-3' (SEQ ID NO 3); JNK2 pool siRNA 5'-CCGUGAACUCGUCCUCUUAAA-3' (SEQ ID NO 4) and 5'-GUGAUGGACUGG-GAAGAAA-3' (SEQ ID NO 5); JNK3 pool siRNA 5'-GAAAGAACUUAUCUTACAA-3' (SEQ ID NO 6) and 5-CCAGUAACAUUGUAGUCAA-3 (SEQ ID NO 7) (Björkblom, B., et al, J. Biol. Chem. 283: 19704-19713 (2004).

siRNA can be administered to a subject by methods known to skilled artisans, for example as set forth in Sohail, M., ed., Gene Silencing by RNA Interference: Technology and Application, CRC Press LLC, Boca Raton, Fla., 2005; Schepers, U., RNA Interference in Practice: Principles, Basics, and Methods for Gene Silencing in *C. elegans, Drosophila*, and Mammals, Wiley-VCH Verlag GmbH & Co., Weinheim 2005; and Engelke, D., RNA interference (RNAi) Nuts & Bolts of RNAi Technology, DNA Press LLC, 2003.

The inventors also have developed methods of screening for compounds or salts thereof that inhibit MLK-family kinases such as dual leucine-zipper-bearing kinase (DLK). In various embodiments, these methods can comprise contacting, in vitro or in vivo, at least one mammalian cell that expresses at least one member of the mixed lineage kinase (MLK) family such as dual leucine-zipper-bearing kinase (DLK) with a candidate agent, and detecting a decrease in MLK activity in the cell, such as a decrease in DLK activity in the cell. A decrease in kinase activity can be detected by any kinase assay known to skilled artisans, such as, for example, detecting a decrease in incorporation of phosphate into a downstream target of a kinase, as measured by, for example, incorporation of a radioisotope such as $^{32}P$. In other embodiments, these methods can comprise contacting, in vitro or in vivo, at least one mammalian cell that expresses at least one MLK and at least one C-Jun N-terminal kinase (JNK) with a candidate agent, and detecting a decrease in activity of the at least one MLK or the at least one JNK activity in the cell. Screening methods can also involve assaying a biological response. In various configurations, these methods comprise providing a neuronal culture comprising a plurality of axons; contacting the culture with a candidate compound and with an axon degeneration-triggering agent; and comparing axonal degeneration in the culture to a control culture comprising the axon degeneration-triggering agent but not the candidate compound. Axonal degeneration can be observed and quantified using, for example, the methods described in the Examples below.

Axon degeneration is a shared feature of many neuropathological conditions. The protective effects of Wld$^s$/Nmnat over-expression and proteasome inhibition indicate that there is an intrinsic axon self-destruction program, but the components of this program had not been previously identified. The present inventors have now shown that the MAP3K DLK and its downstream MAPK JNK are critical factors in the axon degeneration program. Genetic deletion of wnd/DLK in flies, DLK in mice, and pharmacological inhibition of JNK all diminish axotomy-induced Wallerian degeneration. Thus, the conceptually and morphologically similar but distinct processes of apoptosis and axon degeneration share some molecular components. This JNK pathway acts within neurons as injured axons commit to degenerate, rather than controlling the neuron's pre-injury competence to degenerate or the execution phase of the degeneration program. Inhibition of this pathway also decreases axon degeneration in response to the chemotherapeutic agents such as vincristine, whose dose-limiting side effects include neuropathy, suggesting that a common active axon self-destruction program orchestrates axon breakdown in response to multiple insults. Furthermore, inhibiting Wallerian degeneration through inhibition of the DLK/JNK pathway permits the administration of higher doses of such chemotherapeutic agents.

The methods and compositions described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999; Sullivan, W., et al., *Drosophila* Protocols, Cold Spring Harbor, N.Y., 2000; Sioud, M., ed Ribozymes and siRNA Protocols, New York, Springer-Verlag, 2004; Sohail, M., ed., Gene Silencing by RNA Interference: Technology and Application, CRC Press LLC, Boca Raton, Fla., 2005; Schepers, U., RNA Interference in Practice: Principles, Basics, and Methods for Gene Silencing in *C. elegans, Drosophila*, and Mammals, Wiley-VCH Verlag GmbH & Co., Weinheim 2005; and Engelke, D., RNA interference (RNAi) Nuts & Bolts of RNAi Technology, DNA Press LLC, 2003. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995): Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. These publications are incorporated herein by reference, each in its entirety.

As used herein, the singular forms "a", "an" and "the" are intended to include the plural forms as well, unless the context indicates otherwise. The following examples are illustrative and are not intended to be limiting to the scope of any claim.

EXAMPLES

The following examples are intended to be illustrative and are not intended to be limiting of the scope of any claim.

Example 1

Figure 1:
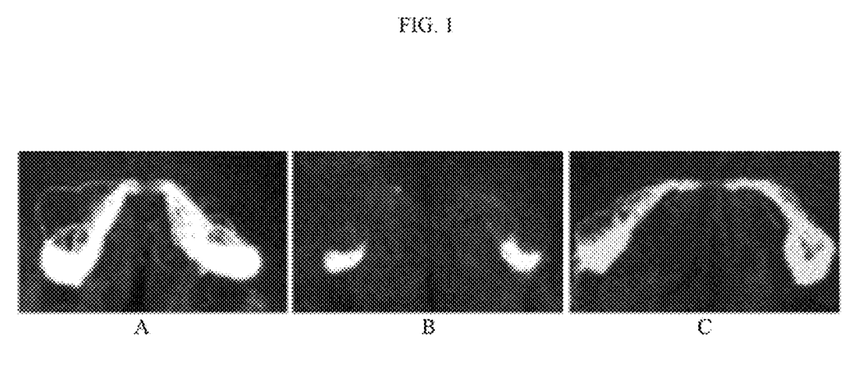
FIG. 1 illustrates that Wallerian degeneration is delayed in Wnd/DLK mutant *Drosophila*.

This example illustrates that DLK is a component of the molecular pathway that promotes axon degeneration, using a well-established *Drosophila* axon degeneration model (Hoopfer, E. D., et al., Neuron, 50: 883-895 (2006); Mac- Donald, J. M., et al., Neuron. 50: 869-881 (2006)). This example further demonstrates that Wallerian degeneration is delayed in Wnd/DLK mutant flies, and that Wnd is required for normal axon degeneration in *Drosophila*. FIG. 1A presents non-axotomized ORN axons expressing GFP; FIG. 1B presents degenerated WT axons 24 hrs. post-axotomy. FIG. 1C presents Wnd/DLK mutant axons 24 hrs. post-axotomy.

In this example, the inventors expressed green fluorescent protein (GFP) in a subpopulation of olfactory receptor neurons (ORNs). ORN cell bodies are located peripherally in the antennae, and their axons extend into the brain and terminate glomeruli of both the ipsilateral and contralateral antennal lobes, which are connected by a commissure (FIG. 1A). To sever these axons and induce axon degeneration, the antennae were surgically removed in this paradigm. Most wild-type axons degenerate within 24 hours, and this degeneration can be delayed by expressing the Wld$^s$ (Hoopfer, E. D., et al., Neuron, 50: 883-895 (2006)) in the ORNs. The degree of degeneration can be scored based on the presence or absence of the commissure formed by the ORN axons connecting the two lobes (Hoopfer, E. D., et at, Neuron, 50: 883-895 (2006)). In these experiments, mutants in the *Drosophila* ortholog of DLK, wnd, have substantially diminished axon degeneration compared to control flies (FIG. 1B,C). The commissure was visible in 4 out of 32 control flies and 18 out of 27 Wnd/DLK mutant flies (Chi-square, p<0.001). Wnd is therefore required for normal axon degeneration in *Drosophila*.

Example 2

This Example illustrates that normal axon degeneration in response to injury such as axotomy or a toxic chemical such as a cancer chemotherapeutic requires DLK in mammalian neurons.

Figure 2:
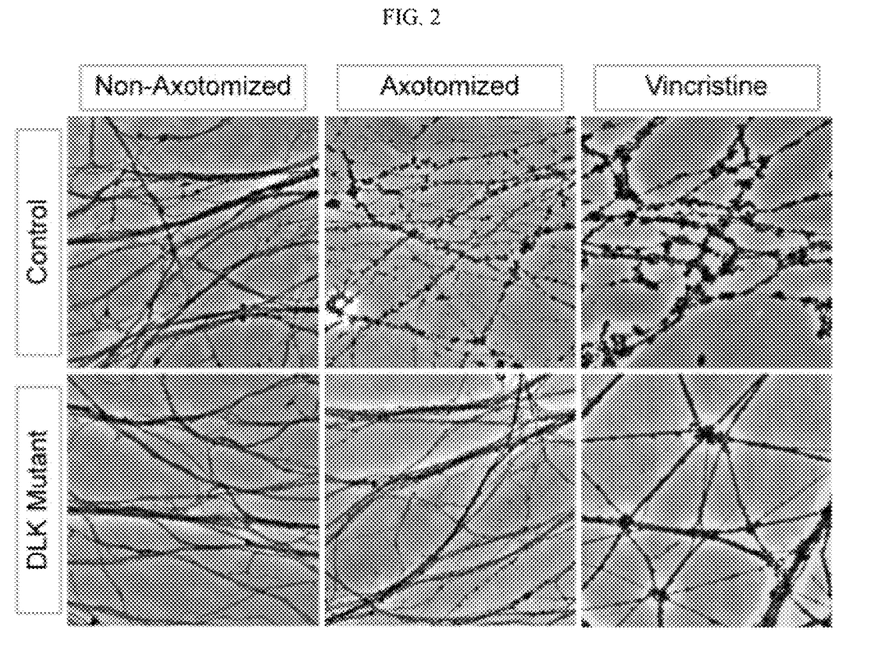
FIG. 2 illustrates that normal axon degeneration in response to axotomy and vincristine requires DLK.

In these experiments, the inventors cultured embryonic mouse dorsal root ganglion cells (DRGs) for 14-16 days to allow their axons to radiate from the central core of cell bodies before severing the axons with a micro-scalpel. FIG. 2 shows phase contrast images of DRG axons from DLK mutants and littermate controls. Axotomized DLK mutant axons have a 65%+/−3.2% (se) decrease in degeneration index (DI) relative to controls (p<0.0001, n=8 individual axotomized DRG cultures per condition, t-test). Vincristine treatment induces 59%+/−6.3% (se) less DI in DLK mutants relative to controls (p<0.002, n=7 DRG cultures per condition, t-test). As shown in FIG. 2, after 24 hours, transected wild-type axons are dramatically degenerated. The initially smooth and continuous axonal processes become rough and irregular axon fragments. The extent of axon breakdown was quantified by measuring the fraction of axonal area occupied by fragmented axons (degeneration index, DI). When cultures from DLK mutants and littermate controls were axotomized, degeneration of the mutant axons was significantly diminished (FIG. 2). Because non-neuronal cells are eliminated in this DRG culture system, we concluded that DLK must be required within neurons themselves for the normal axon degenerative response. Furthermore, the identification of loss-of-function mutants with decreased axon degeneration in both flies and mice demonstrates that axon degeneration is an active process driven in pan by an evolutionary conserved pathway that includes DLK/wnd.

To investigate whether DLK participates in such a common pathway, we assessed the response of DLK mutant DRC neurons to vincristine toxicity. In cultured DRG neurons, applying vincristine triggers an axon degeneration that is morphologically similar to that induced by axotomy (Wang, M. S., et al., J. Neuropathol. Exp. Neurol. 59: 599-606 (2000)) (FIG. 2). However, the present inventors demonstrate that reducing DLK expression or activity protects axons from vincristine toxicity, with a significantly decreased degenerative response relative to control axons (FIG. 2). Hence, DLK promotes axon degeneration in response to both axotomy and neurotoxin exposure. These results indicate that DLK is a component of a common axon self-destruction pathway utilized by both axotomy- and vincristine-induced axon degeneration.

Example 3

This example illustrates that inhibition of JNK during the first three hours of axotomy decreases axonal degeneration.

In these experiments, to determine whether the axon degeneration pathway requires either JNK or p38, we used pharmacological inhibitors of each MAP kinase in the DRG axotomy model. Wild-type DRG cultures were treated with the JNK inhibitor SP600215 and the p38 inhibitor SB203580 starting from 24 hours before axotomy and for the remainder of the experiment.

Figure 3:
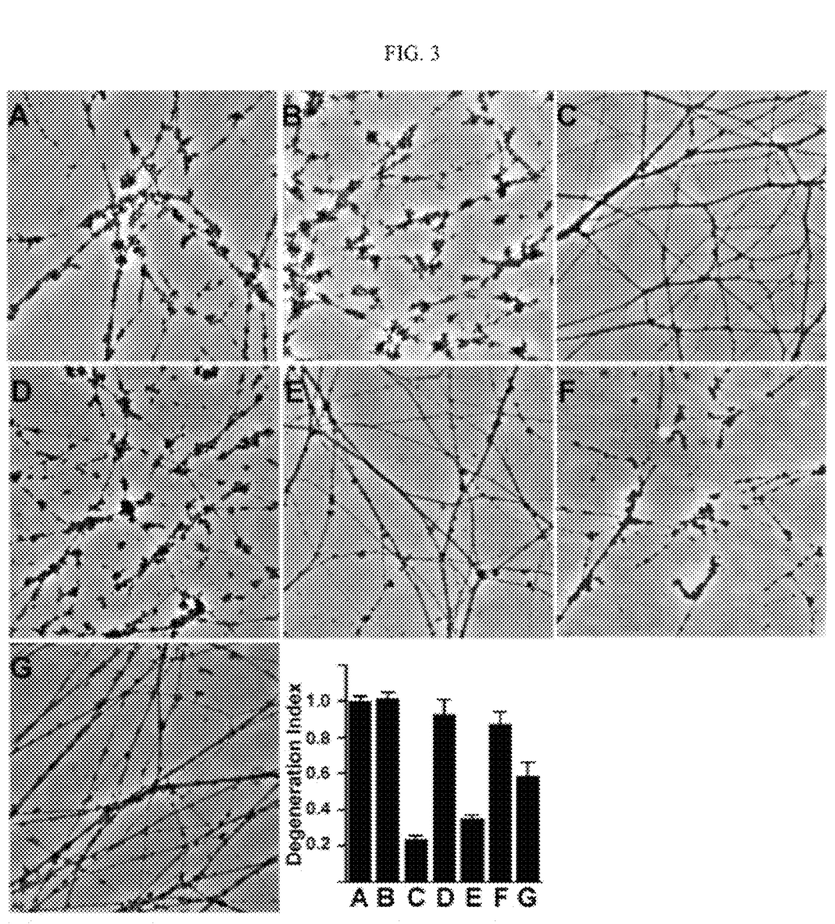
FIG. 3 illustrates that inhibition of JNK during the first three hours of axotomy decreases axonal degeneration.

Phase contrast images of DRG axons 24 hours post-axotomy are shown in FIG. 3. Unless noted, vehicle and inhibitors were added 24 hours pre-axotomy and left on for the duration of the experiment. FIG. 3A: Vehicle (DMSO). FIG. 3B: SB203580 (P38 inhibitor). FIG. 3C: SP600215 (JNK inhibitor). FIG. 3D: SP600215 added 24 hr pre-axotomy, and removed just before axotomy. FIG. 3E: SF600215 added concurrently with axotomy. FIG. 3F: SP600215 added 3 hours post-axotomy. FIG. 3G: SP600215 added concurrent with axotomy and removed 3 hours post-axotomy. Conditions C, E, and G are significantly less degenerated than A (p<0.001, ANOVA, posthoc Tukey's test, n>7 individually axotomized DRG cultures per condition).

Inhibition of JNK, but not p38, decreased degeneration of DRG axons following axotomy (FIG. 3B, FIG. C). Thus JNK, like DLK, is a component of an intrinsic pathway that promotes axon degeneration.

Axon degeneration is hypothesized to comprise at least three distinct phases—competence to degenerate, much of which is determined transcriptionally before axotomy, commitment to degenerate, which occurs in the substantial delay period between injury and axon fragmentation, and the execution phase, when axons fragment (Saxena, S., et al., Prog. Neurobiol. 83: 174-19 (2007)). If JNK's primary role is to promote competence to degenerate, for instance by promoting the expression of pro degenerative factors that are activated after injury, then JNK activity would be required prior to axotomy. We found that this is not the case since application of the JNK inhibitor 24 hours prior to axotomy followed by a wash just before axotomy is not protective (FIG. 3D). In contrast, JNK inhibition started concurrently with axotomy is protective (FIG. 3E). JNK therefore does not control the axon's pre-injury competence to degenerate, but instead it is required in the severed axon itself to promote axon degeneration.

One hallmark of Wallerian degeneration is the substantial delay between the onset of axonal injury and the initiation of rapid axon breakdown, suggesting that a signaling pathway commits the axon to a breakdown program during this delay. To assess whether JNK is involved in the commitment or execution phase of axon breakdown, we added a JNK inhibitor 3 hours after axotomy, which is approximately 12 hours before substantial fragmentation begins. We found that inhibiting JNK beginning 3 hours post-axotomy, and continuing for the rest of the experiment in order to span the transition to the execution phase, did not decrease axon degeneration (FIG. 3F). Thus, JNK inhibition during the execution phase is not sufficient to decrease degeneration. We next investigated if inhibiting JNK only during the early phase is sufficient to decrease axon degeneration. We found that when the JNK inhibitor is added concurrently with the axotomy and then washed off 3 hours post-axotomy, axon degeneration is decreased (FIG. 3G). Thus, inhibition of JNK during this early period, the hypothesized commitment phase, is both necessary and sufficient to decrease axon degeneration.

Example 4

This Example illustrates that DLK mutant mice have decreased Wallerian degeneration in vivo.

There are many differences between in vitro and in vivo models of axon degeneration, and manipulations that diminish degeneration in vitro do not always show the same effect in vivo (Conforti, L., et al., Cell Death Differ. 14: 116-127 (2007)). We therefore investigated whether DLX plays a role in axon degeneration in vivo in mice. Sciatic nerve transection is a simple and well-characterized in vivo model of Wallerian degeneration. Most wild-type axons degenerate within 52 hours post-transection (Beirowski, B., et al., Neurosci. Methods. 134: 23-35 (2004)).

Figure 4:
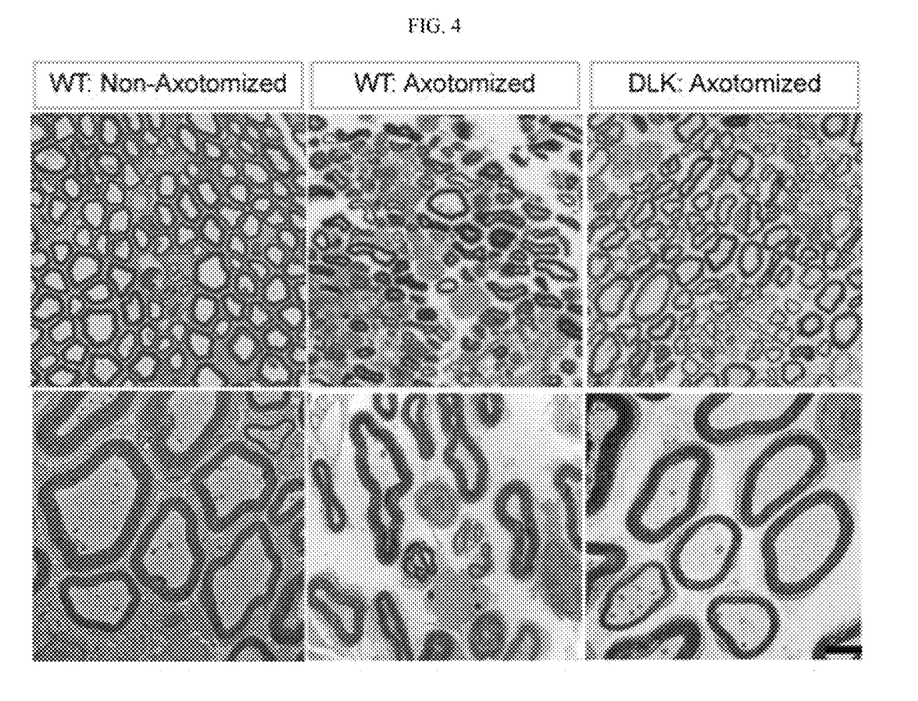
FIG. 4 illustrates that DLK mutant mice have decreased Wallerian degeneration in vivo.

FIG. 4 shows sciatic nerve cross-sections distal to the axotomy stained with Toluidine blue (top row) or imaged by EM (bottom), As shown in FIG. 4, 52 hours post-axotomy. DLK mutants have 208%+/−22% (se) axons per µm² compared to wild-type (p<0.007, t-test, n=4 wild-typo sciatic nerves and 5 DLK mutant sciatic nerves). By EM, mitochondria and microtubules are abundant in the axotomized DLK mutants but not in the axotomized wild-types. In the DLK mutants, however, many axons are spared. We find a more than two-told increase in the number of non-collapsed axonal sheaths from sciatic nerve sections of DLK mutants distal to the axotomy site. In wild-type axons distal to the axotomy, electron microscopic analysis reveals degenerating myelin sheaths, collapsed axonal sheaths, and few recognizable mitochondria or microtubules in the remaining axons. In the DLK mutants, these pathological features are much less prominent, with less degeneration of the surrounding myelin and many more axons containing mitochondria and microtubules (FIG. 4). The finding that DLK is required in vivo for normal axon degeneration validates the relevance of our in vitro results and demonstrates that the DLK pathway provides a therapeutic target for mitigating axon degeneration. EM scale bar=2 µm.

All publications, patents, patent applications and other references cited herein are incorporated by reference in their entirety as if each individual publication, patent, patent application or other reference were specifically and individually indicated to be incorporated by reference.

What is claimed is:

1. A method of mitigating an axonal degeneration in a mammal, the method comprising intraocular administration of an siRNA directed against expression of dual leucine-zipper-bearing kinase to a mammal in need thereof in an amount effective to inhibit axonal degeneration in diseased and/or injured neurons.

2. A method in accordance with claim 1, wherein the axonal degeneration comprises Wallerian degeneration.

3. A method in accordance with claim 1, wherein the axonal degeneration is an optic disorder that is hereditary or congenital or associated with a neurodegenerative disease, and which is selected from the group consisting of a motor neuron disease, a neoplasia, an endocrine disorder, a metabolic disease, a nutritional deficiency, atherosclerosis, an autoimmune disease, a mechanical injury, a chemical injury, a drug-induced injury, a thermal injury, a radiation injury, a nerve compression, a retinal nerve disorder, an optic nerve disorder, a mitochondrial dysfunction, a progressive dementia, a demyelinating disease, ischemia, stroke, an infectious disease and an inflammatory disease.

4. A method in accordance with claim 3, wherein the axonal degeneration is an axonal degeneration induced by a cytotoxic anticancer agent.

5. A method in accordance with claim 3, wherein the optic nerve disorder is selected from the group consisting of glaucoma, retinal ganglion degeneration, optic neuritis, optic degeneration, macular degeneration, ischemic optic neuropathy, traumatic injury to the optic nerve, hereditary optic neuropathy, metabolic optic neuropathy, optic neuropathy due to a toxic agent, optic neuropathy caused by an adverse drug reaction and optic neuropathy caused by a vitamin deficiency.

* * * * *

SEQUENCE LISTING

<160> NUMBER OF SEQ ID NOS: 7

<210> SEQ ID NO 1
<211> LENGTH: 19
<212> TYPE: RNA
<213> ORGANISM: Mus musculus

<400> SEQUENCE: 1
gaauguccua ccuucucua                                                    19

<210> SEQ ID NO 2
<211> LENGTH: 19
<212> TYPE: RNA
<213> ORGANISM: Mus musculus

<400> SEQUENCE: 2
ggaaagaacu gauauacaa                                                    19

<210> SEQ ID NO 3
<211> LENGTH: 19
<212> TYPE: RNA
<213> ORGANISM: Mus musculus

<400> SEQUENCE: 3
gaagcaaacg ugacaacaa                                                    19

<210> SEQ ID NO 4
<211> LENGTH: 21
<212> TYPE: RNA
<213> ORGANISM: Mus musculus

<400> SEQUENCE: 4
ccgugaacuc guccucuuaa a                                                 21

<210> SEQ ID NO 5
<211> LENGTH: 19
<212> TYPE: RNA
<213> ORGANISM: Mus musculus

```
<400> SEQUENCE: 5
gugauggacu gggaagaaa                                          19

<210> SEQ ID NO 6
<211> LENGTH: 19
<212> TYPE: RNA
<213> ORGANISM: Mus musculus

<400> SEQUENCE: 6
ggaaagaacu uaucuacaa                                          19

<210> SEQ ID NO 7
<211> LENGTH: 19
<212> TYPE: RNA
<213> ORGANISM: Mus musculus

<400> SEQUENCE: 7
ccaguaacau uguagucaa                                          19
```